(12) United States Patent
Flach et al.

(10) Patent No.: US 7,085,606 B2
(45) Date of Patent: Aug. 1, 2006

(54) EPICARDIAL ELECTRODE

(75) Inventors: Erhard Flach, Berlin (DE); Gerhard Hahnke, Berlin (DE)

(73) Assignee: Biotronik GmbH & Co., KG, Berlin (DE)

( * ) Notice: Subject to any disclaimer, the term of this patent is extended or adjusted under 35 U.S.C. 154(b) by 104 days.

(21) Appl. No.: 10/845,686

(22) Filed: May 14, 2004

(65) Prior Publication Data

US 2004/0267343 A1 Dec. 30, 2004

(30) Foreign Application Priority Data

May 15, 2003 (DE) ................ 103 23 016

(51) Int. Cl.
*A61N 1/00* (2006.01)
(52) U.S. Cl. .............. 607/129; 607/115; 606/41
(58) Field of Classification Search ............ 607/129, 607/152, 119, 115, 116, 128, 130, 131; 606/41, 606/32, 51, 585
See application file for complete search history.

(56) References Cited

U.S. PATENT DOCUMENTS

| | | | | | |
|---|---|---|---|---|---|
| 3,999,555 | A | * | 12/1976 | Person | 607/130 |
| 4,142,530 | A | * | 3/1979 | Wittkampf | 607/116 |
| 4,144,890 | A | | 3/1979 | Hess | |
| 4,235,246 | A | * | 11/1980 | Weiss | 607/131 |
| 4,282,886 | A | * | 8/1981 | King | 607/130 |
| 4,357,946 | A | * | 11/1982 | Dutcher et al. | 607/131 |
| 4,424,818 | A | * | 1/1984 | Doring et al. | 607/130 |
| 4,607,644 | A | * | 8/1986 | Pohndorf | 450/61 |
| H356 | H | * | 11/1987 | Stokes et al. | 607/126 |
| 5,304,203 | A | * | 4/1994 | El-Mallawany et al. | 606/207 |
| 5,514,174 | A | * | 5/1996 | Heil et al. | 607/128 |
| 5,545,207 | A | * | 8/1996 | Smits et al. | 607/130 |
| 5,683,447 | A | | 11/1997 | Bush et al. | |
| 5,713,919 | A | * | 2/1998 | Lahr | 606/207 |
| 5,871,532 | A | * | 2/1999 | Schroeppel | 607/128 |

FOREIGN PATENT DOCUMENTS

| | | |
|---|---|---|
| EP | 0134367 | 3/1985 |
| WO | WO 03/092797 | 11/2003 |

* cited by examiner

*Primary Examiner*—Robert Pezzuto
*Assistant Examiner*—Shevon Johnson
(74) *Attorney, Agent, or Firm*—Hahn Loeser & Parks, LLP; John J. Cunniff (57) ABSTRACT

An epicardial electrode which is suitable, in particular, for use with a cardiac stimulation device, comprises an electrode body which has a stimulation surface adapted to bear against the cardiac tissue and to stimulate a part of the heart, that is to say a partial region of the heart, and at least one fixing element for fixing the stimulation surface to the cardiac tissue. The at least one fixing element is adapted for engagement into the cardiac tissue. The epicardial electrode can be secured to the outside and in particular to the outer skin of the cardiac muscle (epicardium) without being sewn to the cardiac muscle like a patch electrode. Only the fixing element has to be brought into engagement with the cardiac tissue.

17 Claims, 5 Drawing Sheets

Epicardial electrode, minimally intensive

Test electrode V526 epicardial electrode viewing on to the actuating eyes of the claws in the retracted position

Fig.4 epicardial electrode in a view on to the stimulation surfaces with retracted claws

Fig.5 different and indifferent poles

Fig.6 different pole with pair of extended claws

Fig.7

Epicardial electrode, minimally intensive

Test electrode V527 overall view of the applicator tool

Fig.8 applicator tool in position with
extended claws and closed
electrode holding clips applicator tool in position with
extended claws and closed
electrode holding clips

Fig.9   Fig.10 applicator tool in position with extended claws
and open electrode holding clips

Fig.11

Epicardial electrode, minimally intensive

Electrode with applicator instrument electrode and applicator
instrument with extended
claws and closed holding clips

Fig.12 electrode and applicator
instrument with retracted
claws and closed holding clips

Fig.15 electrode and applicator
instrument with extended
claws and closed holding clips

Fig.13 electrode and applicator
instrument with retracted
claws and closed holding clips

Fig.16 electrode and applicator
instrument with extended
claws and closed holding clips

Fig.14

EPICARDIAL ELECTRODE

This application claims the benefit of German Patent Application Serial No. 103 23 016.5 filed May 15, 2003.

BACKGROUND OF THE INVENTION

The present invention concerns an epicardial electrode, that is to say, an electrode which is adapted to be fitted to the outside of the cardiac muscle, for a heart stimulation device such as for example a defibrillator or a cardiac pacemaker.

BACKGROUND OF THE ART

Supplying electrical signals as stimulation signals in order for example to restore the cardiac rhythm or to keep the rhythm of the heartbeat stable is a medical therapy which has long been in use. For that purpose, cardiac pacemakers but also implantable defibrillators are fitted into the thorax of a patient, for producing the electrical signals as required by means of an internal power source such as a battery. The signals are then passed to a specific location of the heart, which is dependent on the medical application, by way of an electrode line, at the end of which, that is remote from the cardiac pacemaker (in this connection reference is also made to the distal end of the electrode line), is arranged an electrode.

Depending on the respective purpose of the therapy, the electrode may be a unipolar electrode or a bipolar electrode. The term unipolar electrode is used to denote an electrode comprising a single pole, referred to as the different pole, which emits the stimulation pulses. A reference electrode, with what is referred to as an indifferent pole, is associated with the unipolar electrode. The reference electrode, which is also referred to as the indifferent electrode, is frequently formed by the casing of the stimulation device or a patch electrode which is arranged at the outer skin of the cardiac muscle (epicardium). Electrodes fitted to the outside of the cardiac muscle are also referred to as epicardium electrodes or epicardial electrodes.

In contrast to the unipolar electrode, a bipolar electrode has both a different pole and also an indifferent pole, so that no further electrode is required.

In the state of the art, to provide for stimulation of the apex, that is to say the tip of the heart, which is effected for example to stabilize the cardiac rhythm, an electrode is fixed in the interior of the heart in the region of the apex. In that situation, it is necessary for the electrode line to be passed through the chambers of the heart or through the coronary sinus. An electrode placed in the proximity of the apex of the right cardiac chamber is shown, for example, in U.S. Pat. No. 5,683,447. However the operation of placement of the electrode through the cardiac chambers or the coronary sinus is not without its dangers.

SUMMARY OF THE INVENTION

Therefore an object of the invention is to provide an electrode which reduces the risk to the patient upon placement of the electrode.

A further object of the invention is to provide a suitable insertion instrument for inserting the electrode, according to the invention, into the body.

The first object is attained by an epicardial electrode as set forth in claim 1 and the second object is attained by an insertion instrument as set forth in claim 13. The appendant claims define advantageous configurations of the epicardial electrode and the insertion instrument respectively.

An epicardial electrode according to the invention which is suitable in particular for use with a cardiac stimulation device includes an electrode body which has a stimulation surface adapted to bear against the cardiac tissue and to stimulate a part of the heart, that is to say a partial region of the heart, and at least one fixing element for fixing the stimulation surface to the cardiac tissue. The at least one fixing element is designed to engage into the cardiac tissue.

The epicardial electrode according to the invention can be secured to the outside and in particular to the outer skin of the cardiac muscle (epicardium) without being stitched to the cardiac muscle like a patch electrode. It is only necessary for the fixing element to be brought into engagement with the cardiac tissue. The electrode according to the invention facilitates access to the heart and in particular makes it possible to fit the electrode in a minimally invasive intervention.

In addition the configuration of the stimulation surface such that, in contrast to a patch electrode, only a part, that is to say a partial region of the heart, is stimulated, makes it possible to specifically and targetedly stimulate specific regions of the heart. Thus, the electrode according to the invention can be used for example to stimulate the apex of the heart from the outside of the heart. In this case there is no need to implement placement of the electrode through the chambers of the heart or the coronary sinus.

The possibility of stimulating the apex by placement of the electrode according to the invention without the electrode line needing to be passed through the chambers of the heart or the coronary sinus reduces the risk to which the patient is exposed upon placement of the electrode, in comparison with the state of the art.

Overall therefore the electrode according to the invention facilitates access to the apex of the left-hand part of the heart, which is significant in particular for stimulating the cardiac rhythm and/or for sensing cardiac signals.

In order to permit fixing of the stimulation surface without stitching, the at least one fixing element can be in particular in the form of a claw which can be introduced into the cardiac tissue.

In an advantageous development the claw is designed to be movable in such a way that, for fixing the electrode body to the cardiac tissue, the claw is to be extended from a condition of being retracted into the electrode body for implementing engagement with the cardiac tissue. Then, during insertion of the electrode into the body, the claw can be retracted into the electrode body in order not to hinder the insertion operation. It is only when the electrode has reached its target position in the body that the claw is extended to fix the stimulation surface. That design configuration is particularly advantageous if the claw is arranged completely in the interior of the electrode body, in the position of being retracted thereinto.

In a further configuration of the electrode according to the invention, the electrode body, for receiving the claw, has a passage with an elongate passage portion extending in parallel relationship with the stimulation surface and a passage portion curved in such a way that the passage has an exit opening in the stimulation surface. In addition, at least a part of the claw is of a flexible nature and is arranged in the passage, such that, in the retracted condition of the claw, said part of the claw is disposed in a substantially elongate configuration in the elongate passage portion and in the extended condition of the claw is disposed in the curved passage portion. Upon extension of the claw, the flexible part of the claw passes from the elongate passage portion into the curved passage portion. In that embodiment at least a part of the claw extends in parallel relationship with the stimulation surface, in the retracted condition. The parallel configuration of the part of the claw in the retracted condition permits the claw to be retracted completely into the electrode body and at the same time allows the structural height of the electrode body to be kept relatively small. That is of significance in particular if the dimensions of the electrode are to be kept small in order to facilitate implantation in a minimally invasive intervention.

The claw can, in particular, also have a stiff claw portion which is provided for engagement into the cardiac tissue and which is of an arcuate configuration and which in the retracted condition is disposed in the curved passage portion. The stiffness of the curved claw portion counteracts bending of the claw upon producing the engagement with the cardiac tissue.

In order to ensure that the stimulation surface is particularly securely fixed to the cardiac tissue, the electrode according to the invention advantageously includes a plurality of claws. In particular there can be two mutually oppositely disposed pairs of claws.

In order to simplify implantation in a minimally invasive intervention, an advantageous configuration of the electrode according to the invention provides that associated with each fixing element is an engagement element which permits releasable engagement of an actuating element adapted for actuation of the fixing element. In particular, an engagement element, for example an eye, can be simultaneously associated with a plurality of fixing elements, that is to say for example a plurality of claws. Alternatively, however, each fixing element can also have its own engagement element. The electrode can then be positioned with the actuating element in engagement into the engagement element on the heart. The fixing element is then brought into engagement with the cardiac tissue by means of the actuating element. After engagement with the cardiac tissue has been implemented, engagement of the actuating element into the engagement element is released. The actuating element can then be removed.

In a development of that configuration, the engagement element permits extension of a claw by substantially parallel displacement of the actuating element relative to the stimulation surface, in particular when the electrode body has an elongate passage portion for receiving the claw.

In a further configuration of the epicardial electrode, it has a different pole at the stimulation surface. The different pole can be provided with a reservoir of an inflammation-inhibiting active substance, for example a steroid, in order to inhibit the occurrence of inflammation due to engagement of the fixing element into the cardiac tissue. The appropriate stimulation signals can be supplied to the part of the heart to be stimulated, by means of the different pole. In addition the different pole also permits sensing of electrical signals of the heart, which can be used for example for initiating or triggering stimulation.

In addition to the fixing element the stimulation surface may also include a medical fabric or mesh, for example Dacron, for growing fast to the cardiac tissue. That permits the stimulation surface to be particularly securely fixed to the cardiac tissue.

In accordance with the invention there is also provided an insertion instrument for minimally invasive insertion of an electrode according to the invention into the body, which comprises an actuating mechanism with an actuating element for actuating the at least one fixing element in such a way that engagement of the fixing element with the cardiac tissue is implemented. The insertion instrument, therefore, represents an applicator tool which, besides being used for placement of the electrode, can also be used for producing the condition of engagement. The actuating mechanism can in particular be so designed that it permits extension of at least one claw out of the electrode body.

For the purposes of use for implantable electrodes in which the fixing element employed is in the form of a flexible claw which in the retracted condition is disposed at least partially in a passage portion extending in parallel relationship to the stimulation surface, the actuating mechanism, in an embodiment of the insertion instrument, is so designed that it permits substantially parallel displacement of the actuating element relative to the stimulation surface. Displacement of the actuating element then results in displacement, also in parallel relationship with the stimulation surface, of the engagement element which is connected to the claw, and this in turn results in extension of the claw from the electrode body.

In order to permit the electrode to be securely held during the positioning procedure, the insertion instrument can also be provided with holding clips for holding the implantable electrode upon insertion of the implantable electrode into the body.

BRIEF DESCRIPTION OF THE DRAWINGS

Further features, properties and advantages of the invention will be apparent from the description hereinafter of embodiments by way of example, with reference to the accompanying drawings in which.

DETAILED DESCRIPTION OF THE INVENTION

Figure 1:
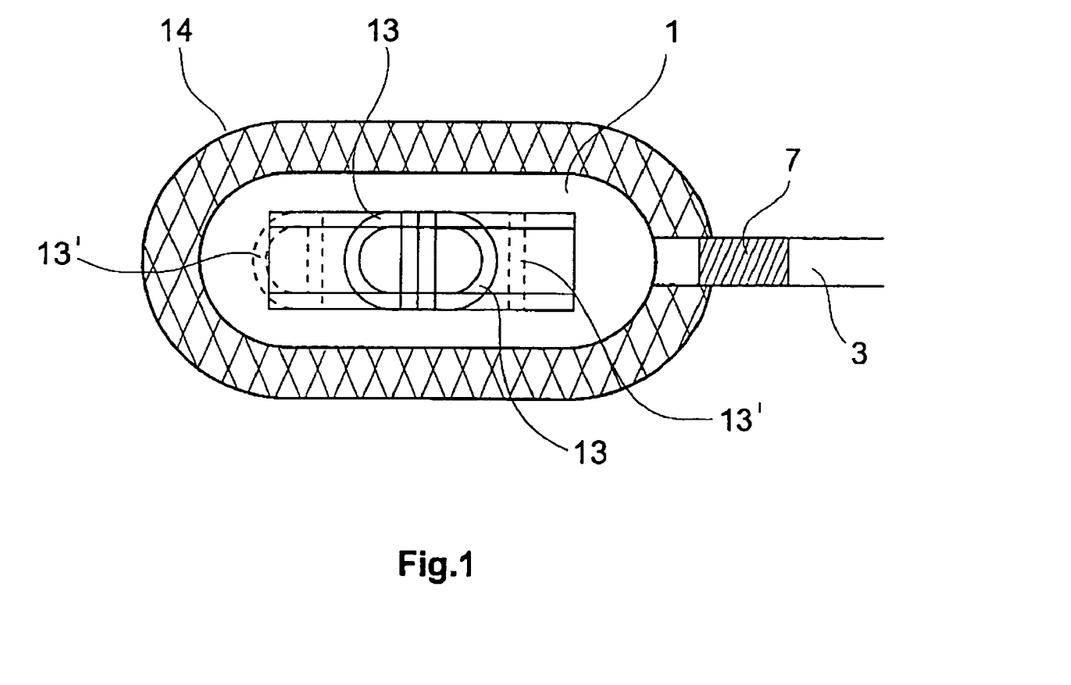
FIG. 1 is a diagrammatic plan view of a first embodiment of the epicardial electrode according to the invention.
Figure 2:
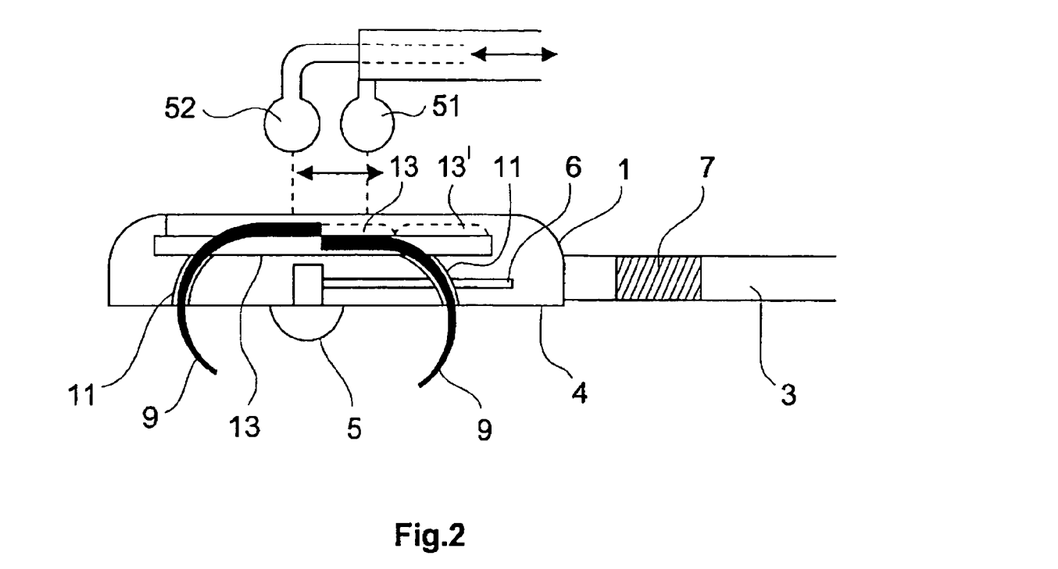
FIG. 2 is a diagrammatic view in vertical section of the first embodiment of the epicardial electrode according to the invention, FIG. 3 diagrammatically shows a first embodiment for the insertion instrument for insertion of the epicardial electrode according to the invention.

FIGS. 1 and 2 are diagrammatic views showing a bipolar epicardial electrode for a cardiac stimulation device as a first embodiment of the epicardial electrode according to the invention. FIG. 1 shows a plan view of the electrode while FIG. 2 shows the electrode in vertical section.

The electrode includes an electrode body 1 which comprises, for example, silicone and which is arranged at the distal end of an electrode line 3, and the underside of which forms the stimulation surface 4 of the epicardial electrode with a different pole 5. The stimulation signals are delivered to the heart by way of the different pole 5, in stimulation operation of the stimulation device (not shown). For that purpose the different pole 5 is connected to the stimulation device by way of an electric line 6 extending through the electrode line 3. In the illustrated embodiment, the indifferent pole 7 is arranged in the form of an annular electrode surface on the electrode line 3.

Admittedly, the electrode shown in FIGS. 1 and 2 is in the form of a bipolar electrode but it can also be in the form of a unipolar electrode. In that case, there is no indifferent pole 7 on the electrode line. Instead, in that case for example the casing of the stimulation device or a patch electrode serves as the indifferent pole.

As fixing elements, the epicardial electrode according to the invention includes four claws 9 (of which two can be seen in FIG. 2), which are arranged in mutually opposite relationship in pairs in passages 11 of the electrode body 1. The claws 9 can be displaced along the passages 11 between two limit positions, wherein the claws are extended from the electrode body in the one limit position which is shown in FIG. 2, so that their claw tips project beyond the stimulation surface 4. Arranged at the ends of the claws 9, which are in opposite relationship to the claw tips, are eyes 13 which are disposed in portions of the passages extending in parallel relationship with the stimulation surface and which permit the engagement of balls 51, 52 of an insertion instrument 50, the balls serving as actuating elements for actuation of the claws. In that arrangement, a common eye is associated with each pair of claws.

The claws 9 can be retracted and extended by relative displacement of the balls 51, 52 in parallel relationship with the stimulation surface 4. In particular, the claws can be moved from a condition in which they are disposed completely within the passages 11 into the extended position. The condition in which the claws are disposed completely in the interior of the passages is indicated by the corresponding, broken-line limit position of the eyes 13. When the stimulation surface 4 bears against the cardiac muscle, the claws 9, upon being extended, penetrate into the cardiac tissue and thereby anchor the electrode in place.

As an optional configuration which permits additional fixing of the epicardial electrode to the cardiac tissue, arranged at the underside of the stimulation surface 4, is a medical Dacron mesh or fabric 14 (not shown in FIG. 2) which permits the electrode to grow fast to the cardiac tissue. In addition, in another optional configuration, the different pole 5 can be provided with a steroid reservoir. The steroid serves to inhibit inflammation which can occur when the claws are introduced into the cardiac tissue.

Admittedly in the described embodiment the electrode includes as fixing elements, four claws 9 which are arranged in mutually opposite relationship in pairs in the electrode body 1, but it is possible to use any number of fixing elements. In that respect the number of fixing elements can be selected for example in dependence on the size of the stimulation surface or the degree of the desired fixing action.

Figure 3:
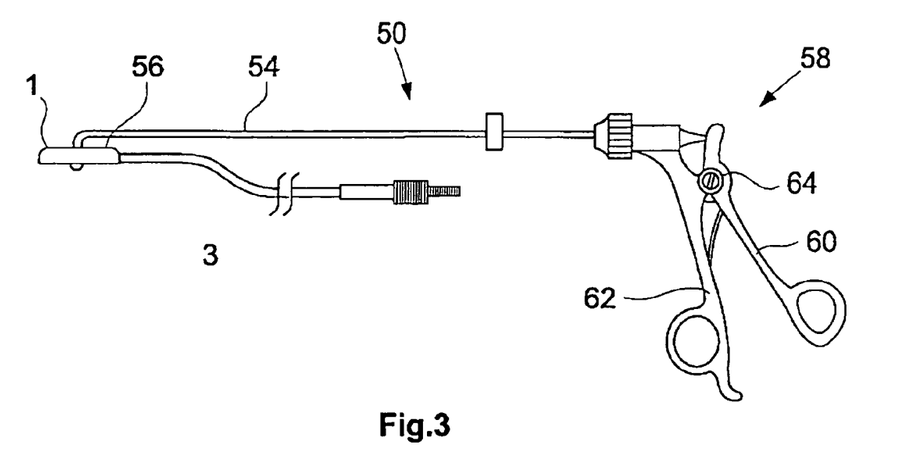

FIG. 3 diagrammatically shows an embodiment of the insertion instrument 50, for insertion of the epicardial electrode according to the invention, into the body. An enlarged view of the distal end of the insertion instrument can be seen in FIG. 2. The insertion instrument 50 includes a hollow tube 54, to the distal end of which is fixed a ball 51 which is adapted for engagement into the eyes 13 of the claws 9. Arranged in the interior of the hollow tube 54 is a rod 56 which can be displaced in the longitudinal direction relative to the hollow tube 54. Disposed at the end of the rod 56 is a second ball 52 adapted for engagement into the eyes 13 of the claws. Displacement of the rod 56 with respect to the tube 54 causes the balls 51 and 52 to move away from each other and towards each other. When in that situation the balls 51, 52 are engaged into the eyes 13 of the claws 9, movement of the balls 51, 52 towards each other results in the claws 9 being extended from the passages 11 while movement of the balls 51, 52 away from each other causes retraction of the claws 9 into the passages 11.

A handle 58 with two handle portions 60, 62 is arranged at the proximal end of the insertion instrument 50. The two handle portions 60, 62 are arranged pivotably relative to each other by way of a pivot 64 and are connected to the rod 56 and the tube 54 respectively, such that the balls 51, 52 move towards each other when the two handle portions 60, 62 are pivoted towards each other and the two balls 51, 52 move away from each other when the two handle portions 60, 62 are pivoted away from each other. The balls 51, 52, the tube 54, the rod 56 and the handle 58 together form an actuating mechanism for retraction and extension of the claws 9.

Besides actuation of the claws 9, the insertion instrument 50 also serves for placement of the electrode which in that situation is held for example by means of the balls 51, 52 on the insertion instrument 50. As soon as the electrode is placed at the correct location of the heart it can be fixed by means of the actuating mechanism. The insertion instrument 50 is removed again after the claws 9 have been extended.

In order to permit the electrode to be held in the placement operation and to permit the insertion instrument 50 to be removed after fixing of the electrode, the top side of the electrode body 1 can have two elongate holes or slots which extend in the direction of displacement of the eyes 13 and which, where the eyes 13 are disposed in the extended condition of the claws, are widened in such a way that the balls 51, 52 can pass through the slots or elongate holes only at that location, that is to say in the extended condition of the claws. Prior to insertion of the electrode the balls 51, 52 are inserted into the eyes 13 when the claws are in the extended condition and then the claws are retracted by actuation of the actuating mechanism. In that case the balls 51, 52 move into those portions of the slots or elongate holes, which do not permit the balls 51, 52 to pass therethrough. The balls 51, 52 can be extracted from the eyes 13 only after extension of the claws, that is to say after the electrode has been fixed in place.

Figure 4:
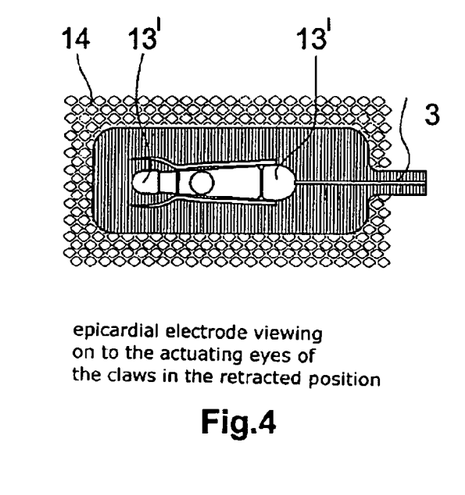
FIG. 4 shows the top side of a second embodiment of the epicardial electrode according to the invention.
Figure 5:
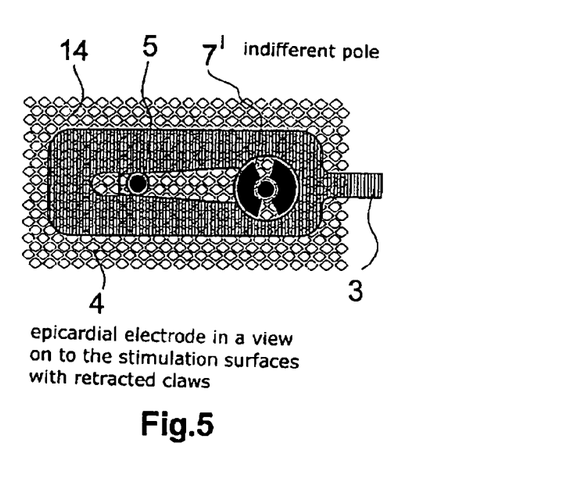
FIG. 5 shows the underside of the second embodiment of the epicardial electrode according to the invention.
Figure 6:
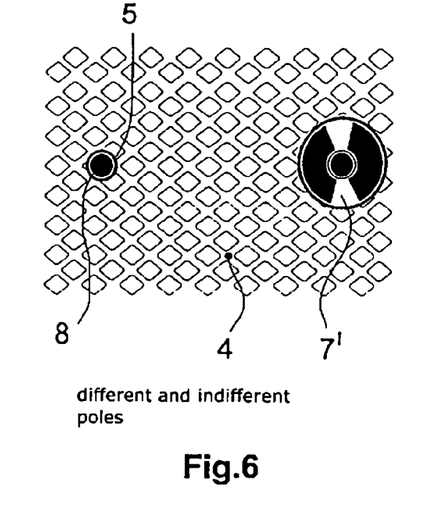
FIGS. 6 and 7 shows details of the underside of the second embodiment of the epicardial electrode according to the invention.
Figure 7:
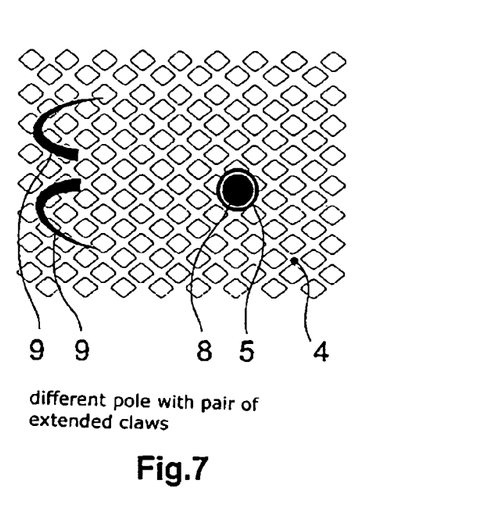

FIGS. 4 through 7 show a second embodiment of the epicardial electrode according to the invention, FIG. 4 being a view on to the electrode body 1 and FIG. 5 being a view on to the stimulation surface 4. FIG. 6 is a view on an enlarged scale of a portion of the stimulation surface 4, which includes the different and the indifferent poles 5 and 7' respectively of the epicardial electrode. FIG. 7 shows the stimulation surface 4 in a view on an enlarged scale, illustrating the different pole 5 and the extended claws 9. Features of the second embodiment which do not differ from those of the first embodiment are denoted by the same references as in the first embodiment.

The second embodiment differs from the first embodiment only in that the indifferent pole 7' is not arranged in the form of an annular electrode surface on the electrode line 3 but is like the different pole 5 on the stimulation surface 4. That makes it possible to achieve good contact between the indifferent pole 7' and the cardiac tissue. However, arranging the indifferent electrode 7' on the stimulation surface 4 increases the size thereof as the spacing between the indifferent pole and the different pole can be about 10 mm or more. In the illustrated embodiment the electrode body 1 is about 4.6 mm high, about 10 mm wide and about 25 mm long. The area of the Dacron mesh or fabric arranged on the stimulation surface is about 14 mm×32 mm.

The claws 9 can comprise, for example, wire and typically are of a diameter of about 0.2 mm. The passages for the claws 9 in the electrode body 1 are then typically of a diameter of about 0.4 mm. The different and the indifferent pole typically are of a diameter of about 1.8 mm and 4.0 mm respectively, the thickness of the different pole being about 0.6 mm and that of the indifferent pole being about 0.3 mm. Disposed at the center of the different pole is a steroid reservoir 8 of a diameter of about 1.0 mm, which contains about 1 mg of a steroid, for example dexamethasone phosphate.

The dimensions set forth in relation to the second embodiment can be applied in respect of their order of magnitude to the first embodiment, except for the length of the electrode body 1 and the dimensions of the indifferent pole 7'. Equally the foregoing information relating to the claw material can also be applied to the first embodiment.

Figure 8:
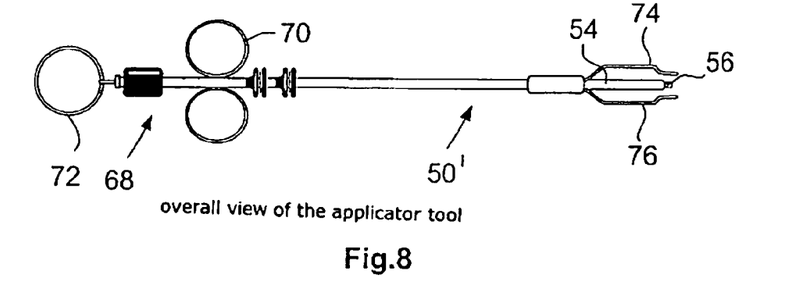
FIG. 8 is an overall view of a second embodiment of the insertion instrument for the epicardial electrode according to the invention.

FIG. 8 shows a second embodiment of the insertion instrument according to the invention. The insertion instrument 50' in the second embodiment corresponds in its structure in principle to that of the first embodiment. Features of the insertion instrument in accordance with the second embodiment, which do not differ from those of the first embodiment, are denoted by the same references in both embodiments.

As a departure from the first embodiment, the handle 68 of the actuating arrangement in the second embodiment for relative displacement of the balls does not include two handle portions which are pivotable relative to each other, but two handle portions 70, 72 which are slidable relative to each other. In addition the insertion instrument 50' of the second embodiment includes two holding clips 74, 76 for holding the electrode during the insertion and fixing procedure. By means of a device provided on the handle 68, the holding clips 74, 76 can be moved selectively into a closed position in which they hold an electrode at the distal end of the insertion instrument or into an open position in which the electrode is not held.

Figure 9:
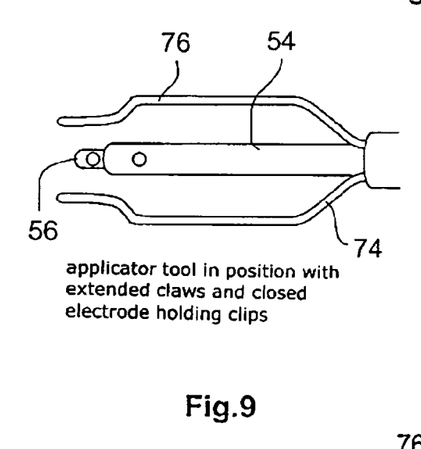
FIGS. 9–11 show the second embodiment for the insertion instrument according to the invention in various positions.
Figure 10:
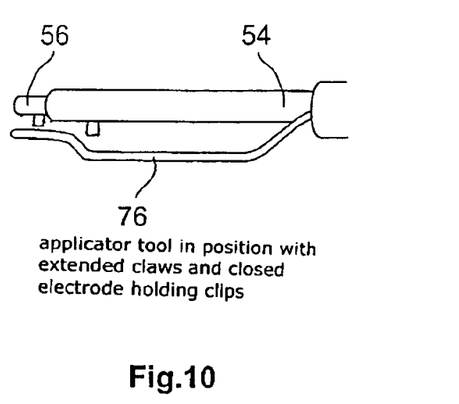
Figure 11:
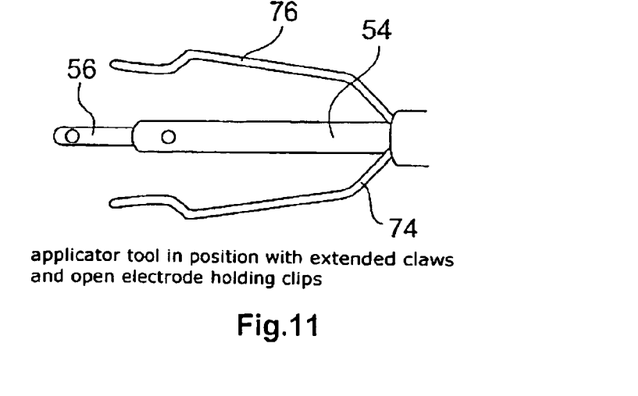

FIGS. 9 and 10 show the distal end of the insertion instrument 50' in the configuration which it adopts when the claws of the electrode are extended and the holding clips 74, 75 are closed. FIG. 11 in contrast shows the distal end of the insertion instrument when the claws are retracted and the holding clips 74, 76 are opened.

Figure 12:
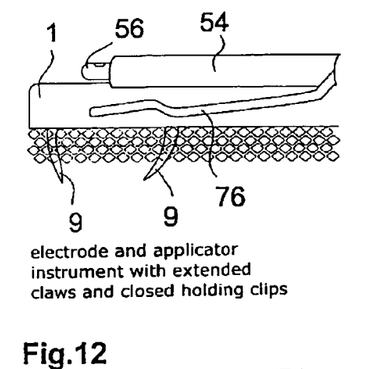
FIGS. 12–16 show the second embodiment of the insertion instrument according to the invention with epicardial electrode arranged thereon in various positions.
Figure 13:
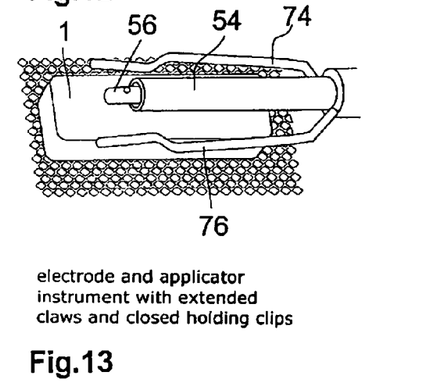
Figure 14:
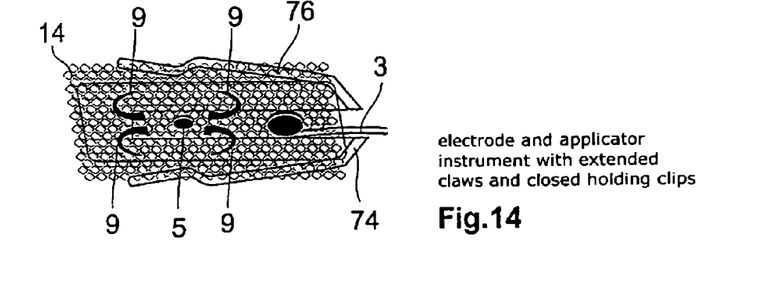
Figure 15:
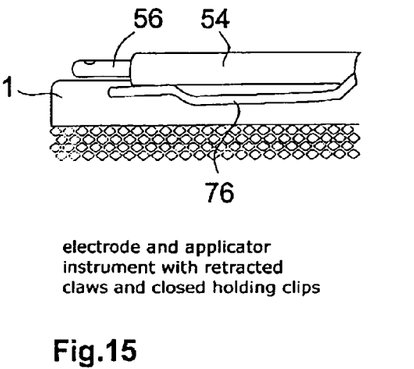
Figure 16:
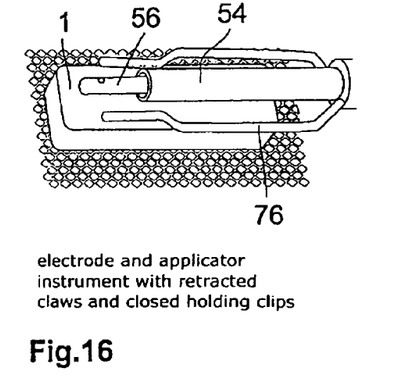

FIGS. 12 through 16 show the insertion instrument 50' in accordance with the second embodiment with closed holding clips 74, 76 and an epicardial electrode held by the holding clips 74, 76. In order to support secure retention of the epicardial electrode by the holding clips 74, 76, the side walls of the electrode body 1 have grooves 16 into which the holding clips 74, 76 engage in the closed condition. While FIGS. 12 through 14 show the electrode and the distal end of the insertion instrument 50' from different angles of view with claws 9 in the extended condition and holding clips 74, 76 in the closed condition, FIGS. 15 and 16 show the electrode and the distal end of the insertion instrument 50' with claws 9 in the retracted condition and holding clips 74, 76 in the closed condition.

When the electrode is held by the holding clips 74, 76 in the insertion and fixing procedure, it is sufficient for the actuating elements, instead of being in the form of balls, to be in the form of simple projections which are suitable for engagement into the eyes 13 of the claws 9 of the electrode as the actuating elements do not need to perform a holding function for the electrode.

What is claimed is:

1. An epicardial electrode for a cardiac stimulation device comprising:

an electrode body having a stimulation surface adapted to bear against cardiac tissue and to stimulate a part of the heart; and at least one fixing element in the form of a claw adapted to be engaged into the cardiac tissue for fixing the stimulation surface to the cardiac tissue, wherein the claw is adapted to be movable such that it is to be extended from a condition of being retracted in the electrode body to provide for engagement with the cardiac tissue, wherein the electrode body has at least one passage with an elongate passage portion extending in parallel relationship with the stimulation surface and a curved passage portion such that the passage has an exit opening in the stimulation surface, and wherein at least a part of the claw is of a flexible nature and is arranged in the passage such that in the retracted condition of the claw, said part of the claw is disposed in a substantially elongate condition in the elongate passage portion and in the extended condition of the claw said part of the claw is disposed in the curved passage portion, wherein at least two of the fixing elements are reversibly extendable from a condition of being retracted in the electrode body to provide for reversible engagement with the cardiac tissue.

2. An epicardial electrode according to claim 1, wherein in the retracted position, the claw is arranged completely in the interior of the electrode body.

3. An epicardial electrode according to claim 1, wherein the claw has a stiff claw portion which is provided for engagement into the cardiac tissue and which is of an arcuate configuration and which is disposed in the curved passage portion in the retracted condition.

4. An epicardial electrode according to claim 1, wherein the stimulation surface includes a medical mesh or fabric for growing fast to the cardiac tissue.

5. An epicardial electrode according to claim 1, comprising a plurality of claws.

6. An epicardial electrode according to claim 5, wherein each fixing element is adapted to be engaged by an engagement element and wherein the engagement element is adapted to permit releasable engagement of an actuating element for actuation of the fixing element.

7. An epicardial electrode according to claim 6, wherein the engagement element is adapted to be displaceable by the actuating element in substantially parallel relationship with the stimulation surface.

8. An epicardial electrode according to claim 7, additionally comprising a different pole on the stimulation surface.

9. An epicardial electrode according to claim 8, wherein the different pole is provided with a reservoir of an inflammation-inhibiting active substance.

10. An insertion instrument for minimally invasive insertion of an epicardial electrode into the body, which comprises an actuating mechanism with at least one actuating element adapted to reversibly actuate more than two fixing elements of the electrode for reversible engagement with cardiac tissue.

11. An insertion instrument according to claim 10, wherein the actuating mechanism is adapted to permit extension of a claw-type fixing element from the electrode body.

12. An insertion instrument according to claim 11, wherein the actuating mechanism is adapted for substantially parallel displacement of the actuating element relative to the stimulation surface.

13. An insertion instrument according to claim 10, additionally comprising holding clips for holding the epicardial electrode upon insertion into the body.

14. An insertion instrument for minimally invasive insertion of an epicardial electrode into the body, which comprises an actuating mechanism with at least one actuating element adapted to reversibly actuate more than two fixing elements of the electrode for reversible engagement with cardiac tissue, wherein the at least one actuating element is in the form of a ball.

15. An insertion instrument according to claim 14, wherein the actuating mechanism is adapted to permit extension of a claw-type fixing element from the electrode body.

16. An insertion instrument according to claim 15, wherein the actuating mechanism is adapted for substantially parallel displacement of the actuating element relative to the stimulation surface.

17. An insertion instrument according to claim 14, additionally comprising holding clips for holding the epicardial electrode upon insertion into the body.

* * * * *